United States Patent [19]

McGreevy

[11] 4,429,694

[45] Feb. 7, 1984

[54] ELECTROSURGICAL GENERATOR

[75] Inventor: Francis T. McGreevy, Aurora, Colo.

[73] Assignee: C. R. Bard, Inc., Murray Hill, N.J.

[21] Appl. No.: 281,005

[22] Filed: Jul. 6, 1981

[51] Int. Cl.³ .......................................... A61B 17/39
[52] U.S. Cl. ........................... 128/303.14; 128/303.17
[58] Field of Search ..................... 128/303.13, 303.14, 128/303.17

[56] References Cited

U.S. PATENT DOCUMENTS

| 3,658,067 | 4/1972 | Bross | 128/303.14 |
| 3,699,967 | 10/1972 | Anderson | 128/303.14 |
| 3,952,748 | 4/1976 | Kaliher et al. | 128/303.17 |
| 3,963,030 | 6/1976 | Newton | 128/303.17 |
| 4,030,501 | 6/1977 | Archibald | 128/303.14 |
| 4,318,409 | 3/1982 | Ooster | 128/303.17 |

OTHER PUBLICATIONS

Sabah, "A High-Frequency Coagulatur . . . ", EEG & Clin. Neurophysiology, vol. 36, No. 3, pp. 311-313, Mar. 1974.

Primary Examiner—Lee S. Cohen
Attorney, Agent, or Firm—Wolf, Greenfield & Sacks

[57] ABSTRACT

A solid-state electrosurgical generator is disclosed which provides output waveforms that are optimized for electrosurgical fulguration. The fulguration output circuitry consists of a radio-frequency tank circuit which is periodically pulsed to produce a periodic damped-sinusoidal output waveform. However, the damping factor is sufficiently low so that many cycles of the waveform occur between periodic input pulses. Although the duty cycle is relatively high compared to prior art devices, cutting and burning effects are prevented by a high impedance output which internally limits fulguration arc current. The fulgurating arc developed by the device is longer and more consistent than that developed by previous devices thereby resulting in superior fulguration.

26 Claims, 12 Drawing Figures

PRIOR ART BOVIE DEVICE

*Fig.6A*
OPEN CIRCUIT

*Fig.6B*
LOADED

PRIOR ART SOLID STATE DEVICE

*Fig.6C*
OPEN CIRCUIT

*Fig.6D*
LOADED

*Fig.6E*
OPEN CIRCUIT

*Fig.6F*
LOADED

Fig.7

ELECTROSURGICAL GENERATOR

FIELD OF THE INVENTION

This invention relates to electrosurgery in general and, in particular, to electrosurgical generators which are capable of performing surgical operations by means of radio-frequency electrical currents.

BACKGROUND OF THE INVENTION

In addition to performing surgical operations on animal tissues by means of mechanical instruments such as scalpels or knives, surgery may also be performed by passing radio-frequency current through animal tissues. There are essentially four main surgical operations that can be electrically performed, depending on the voltage levels and the amount of power applied to the tissue. These operations are typically described as dessication, fulguration, cutting and cutting with hemostasis. Often, dessication and fulguration are described collectively as coagulation.

The high-frequency current used in performing electrosurgical operations is typically generated by means of a radio-frequency generator connected to a power amplifier. The output of the power amplifier is in turn connected to the tissue mass by means of two electrodes. Surgical operations are performed by means of an "active" electrode which introduces the radio-frequency current into the tissue mass.

Since, as mentioned above, electrosurgical effects are primarily dependent on the power and voltage applied, the active electrode typically has a small cross-section to concentrate the power and limit the surgical effects to a small, controlled area. A return path from the tissue mass to the generator for the radio-frequency current is provided by a "passive" or "patient" plate which has a large area to prevent electrosurgical effects from taking place at the current return location. Alternatively, a pair of active electrodes may be used in a "bipolar" mode in which the electrosurgical effects are confined to the sample of tissue between the two electrodes.

A dessication operation is performed by holding the active electrode in firm contact with the tissue. Radio-frequency current passes from the electrode directly into the tissue to produce heating of the tissue by electrical resistance heating. The heating effect destroys the tissue cells and produces an area of necrosis which spreads radially from the point of contact between the electrode and the tissue. Due to the nature of the cell destruction, the necrosis is usually deep.

Depending on the output characteristics of the electrosurgical generator, another surgical effect called fulguration may be obtained by varying the voltage and power applied by the electrosurgical generator. Although fulguration is often confused with dessication, it is a distinctly different operation. In particular, fulguration is typically performed in prior art devices with a waveform which has a high peak voltage but a low duty cycle. If an active electrode with this type of waveform is brought close to a tissue mass and if the peak voltage is sufficient to produce a radio-frequency arc, fulguration occurs at the point where the arc contacts the tissue. Due to the low duty cycle of the fulgurating waveform, the power per unit time applied to the tissue is low enough so that cutting effects due to explosive volatization of cell moisture are minimized. In effect, the radio-frequency arc coagulates the tissue in the immediate vicinity of the active electrode thereby allowing the operating surgeon to seal off blood vessels in the vicinity of the electrode. The fulgurating electrode never touches the surface of the tissue. In contrast to dessication, fulguration is a surface process and the area of necrosis is confined to the surface. Therefore, fulguration can be used where the tissue mass is very thin and the deep necrosis produced by a dessication operation would damage underlying organs and accordingly, is a very useful operation.

With different output characteristics of the electrosurgical generator, still another effect can be produced. Cutting occurs when sufficient power per unit time is delivered to the tissue to vaporize cell moisture. If the power applied is high enough a sufficient amount of steam is generated to form a layer of steam between the active electrode and the tissue. When the steam layer forms, a "plasma" consisting of highly ionized air and water molecules forms between the electrode and the tissue. If the electrosurgical generator can provide sufficient power, a radio-frequency electrical arc develops in the plasma. When this happens the current entering the tissue is limited to an area equal to the cross-sectional area of the arc where it contacts the tissue and thus the power density becomes extremely high at this point. As a result of the locally high power density the cell water volatizes into steam instantaneously and disrupts the tissue architecture—literally blowing the cells apart. New steam is thereby produced to maintain the steam layer between the electrode and the tissue. If the power density delivered to the tissue mass is sufficient, enough cells are destroyed to cause a cutting action to take place. A repetitive voltage waveform, such as a sinusoid, delivers a continuous succession of arcs and produces a cut with very little necrosis and little hemostasis.

It is also possible to achieve a combination of the above effects by varying the electrical waveform applied to the tissue. In particular, a combination of cutting and dessication (called cutting with hemostasis) can be produced by periodically interrupting the continuous sinusoidal voltage normally used to produce an electrosurgical cut. If the interruption is of sufficient duration, the ionized particles in the plasma located between the electrode and the tissue diffuse away, causing the plasma to collapse. When this happens the electrode comes in contact with the tissue momentarily until a new plasma layer is formed. During the time that the electrode is in contact with the tissue it dessicates the tissue thereby sealing off small blood vessels and other bleeders in the vicinity of the electrode.

The four above-described surgical operations thus require the electrosurgical generator to operate into a varying tissue impedance at various power levels. Although many prior art devices have produced satisfactory results with dessication and cutting operations, most prior art electrosurgical generators have failed to produce satisfactory fulguration. In particular, the electrical arcs produced by prior art generators operating in a fulguration mode are rather short in length and duration. As a result the active electrode must be moved very close to the tissue being fulgurized. If the active electrode actually touches the tissue during the fulgurization operation, tissue may cling to the electrode causing tissue damage and fouling of the electrode which then must be cleaned by the operating surgeon. Thus, the spark length of the prior art machines makes them highly unsatisfactory in many situations especially when the tissue being fulgurized is pulsating due to blood flow or in motion due to respiration. This problem is further exacerbated by the tendency of prior art machines to deliver a significant amount of power to the fulgurated area. In order to increase the arc length, many machines have increased the output fulgurating voltage and thus the output power. The high power input causes the the fulgurated tissue to pucker and swell, thereby increasing the probability of electrode contact.

In addition, prior art electrosurgical generators have not been able to satisfactorly fulgurate spongy or vascular tissue such as a spleen or liver. Since these organs virtually ooze blood through their vascular tissue structure it is very difficult to coagulate an incision to produce satisfactory hemostasis. The relatively high output power of the prior art machines actually initiates secondary bleeding under the area of eschar in this type of organ. In addition, if these machines are used on an organ for more than a short time, the high power produced may actually overheat an entire organ by electrical resistance heating to cause serious damage.

Due to the above shortcomings of the prior art, many surgeons have relied to a great extent upon an older electrosurgical generator which produces a fulgurating radio-frequency output by means of a spark gap. These devices are known as "Bovie devices" and typically produce a 12,000–14,000 volt peak-to-peak highly damped sinusoidal waveform when used during fulguration. Although they are relatively old devices they still produce the most satisfactory fulguration waveform. Even though these deivces operate better than most modern solid state devices they still produce fulgurating arcs which are short in length and duration. Also, these units are large and bulky and require continuous maintenance to replace the internal spark gaps. Because of these shortcomings, other surgeons have entirely foregone the fulgurization function of electrosurgical generators, preferring to rely on the machines only for cutting and dessication.

SUMMARY OF THE INVENTION

The foregoing and other problems inherent in the prior art are solved in one illustrative embodiment of an electrosurgical generator which utilizes solid state circuitry to produce the high voltage necessary for fulgurization. Advantageously, the inventive electrosurgical generator produces an arc of sufficient length and duration to avoid the problems encountered with prior art electrosurgical generators.

Specifically, the illustrative fulguration circuitry disclosed herein enhances initial arc formation by producing an open circuit (prior to arc formation) waveform on the active electrode which is a "true" sinusoid in that it contains alternate positive and negative sections of approximately equal amplitudes. The symmetrical waveform advantageously allows an electrical arc to form when the active electrode is further away from the tissue mass than is presently possible with prior art devices.

In addition, in accordance with the invention, the waveform damping factor is adjusted to be as low as possible so that under open circuit conditions many cycles occur before the waveform drops to zero for any significant length of time. The cyclic excursion of the voltage encourages "corona" formation which significantly enhances arc formation. In addition the internal damping is low enough so that even after arc formation, when waveform damping due to output loading occurs, many waveform cycles are still present. Thus the circuitry helps maintain an arc once it is formed by preventing the total diffusion of ionized particles in the plasma between the electrode and tissue away from the area undergoing fulguration. Thus, the effective load impedance is lower enhancing the arc length and promoting more consistent arc formation during each cycle of the oscillating output voltage waveform. The more consistent arcing causes the active electrode tip to become substantially heated by resistance heating, preventing adherence of blood to the electrode tip during fulguration operations.

Further, although the duty cycle of the inventive output waveform is much higher than prior art units, cutting, burning and overheating effects which have plagued the prior art are avoided because the output impedance of the inventive generator is also much higher than prior art units so that fulgurating arc current applied to the tissue in the area of fulguration is limited by the generator internal impedance, resulting in the avoidance of increased necrosis. In addition, fulguration may be peformed for a longer time without danger of overheating. Alternatively, the generator is operated more like a current source with high impedance than a voltage source.

More particularly, one embodiment of the inventive electrosurgical generator output circuit consists of a radio-frequency "tank" output circit which is excited by current pulses delivered through a high-frequency switching circuit. After each pulse, the tank circuit produces a damped sinusoidal waveform. The "Q" factor of the tank circuit is as high as possible resulting in little damping during each period. In addition, the output transformer of the circuit is constructed specially to minimize losses and the component values of the tank circuit are chosen to produce a high impedance output which internally limits output current flow during electrical arcing.

DETAILED DESCRIPTION

Since fulguration effects are produced principally by an electrical arc, the illustrative embodiment described herein produces superior fulguration properties by enhancing arc length and quality. While it is not necessary to fully understand the mechanism of electrical arc discharges in order to understand the operation of the illustrative circuitry, it is helpful to review the physical phenomena which occur during the generation of an electrical arc between an electrode and a tissue mass. The arcing process consists of two distinct steps: the formation of the arc, and the maintenance of the arc after formation. The effective load impedance experiences a large change during arc formation and, accordingly, the electrical conditions governing operation of the fulguration circuit differ greatly between the two stages. The physical phenomena occuring during each stage are complex and only an outline is given below.

When an active electrode at high electrical potential is brought close to a tissue mass at substantially lower potential, before an electrical arc is established, the initial impedance (as seen from the electrode) between the electrode and the tissue mass is relatively high due to the insulating qualities of the air in the electrode-tissue gap.

The electric field gradient in the air gap between electrode and tissue increases as the gap width decreases. The increasing electric field causes transient currents to begin flowing between the electrode and tissue which are fortuitously initiated by electrons generated by cosmic ray collisions or photoemissions. Most of these electrons are immediately absorbed, but some are very rapidly accelerated towards the field sources with opposite charge. As the electric field strength increases, some of the free electrons and ionized air molecules are accelerated to a sufficient velocity before absorption to ionize other molecules by a variety of mechanisms including single and multiple impact ionization and other physical effects. As the electric potential applied to the gap increases to a value equal to or greater than a characteristic value designated as the "sparking potential" the current created by the movement of oppositely-charged particles becomes self-sustaining and a high voltage "corona" develops. At first the numbers of charged particles is relatively small and thus the impedance between the electrode and tissue mass remains high.

However, as the electrode-tissue mass distance is further decreased, the increase in electric field gradient causes increased acceleration of the electrons and ionized air molecules so that additional ionization processes take place and large numbers of electrons are free. The newly freed electrons also produce additional ionization effects and an electron "avalanche" occurs resulting in the establishment of an electrical arc between the electrode and the tissue mass. At this point, the current density becomes very high and the voltage between the electrode and tissue mass decreases to a low value. A small increase in voltage will cause a large increase in current because the effective impedance of the highly ionized "plasma" between the electrode and the tissue mass is very low. Therefore, the current passing through the electrical arc is limited mainly by the impedance of the output circuitry in the fulguration apparatus and the effective load impedance.

In order to provide a satisfactory fulguration arc, it has been found, in accordance with the invention, that the waveform produced by the generator before electrical arc formation must be significantly different from that produced after arc formation. Specifically, the electrosurgical generator must be able to control the formation of the arc when the effective load impedance is relatively high (before arc formation) and also must be able to control the amount of current applied to the tissue mass after arc formation in order to limit cutting and burning effects. It has also been found, as will be discussed in detail below, that a preferred electrosurgical generator used for fulguration must be capable of producing the following effects:

a. In an "open circuit" condition (driving into a high impedance before arc formation), the generator must provide a waveform which is symmetrical around zero voltage during each cycle, i.e. the waveform must have a positive portion followed by a negative portion of approximately the same amplitude followed by a positive portion, et cetera. Alternatively, the dominant frequency produced at the output must be the fundamental frequency of oscillation with the higher-order harmonics sufficiently suppressed so that the waveform is symmetric;

b. Also, in an "open circuit" condition (driving into a high impedance before arc formation) and the "loaded" condition (driving into the tissue impedance after arc formation) the waveform produced by a fulguration generator must have as low a damping factor as possible so that as many cycles of the waveform are present before the amplitude of the waveform approaches zero. Alternatively, the "Q" factor of an output oscillator "tank" circuit must be high; and c. because the above two conditions produce a waveform with a relatively high duty cycle, the output impedance of the generator must be high to limit the current developed in the electrical arc to reduce cutting and burning effects. Alternatively, the generator must be operated more like a current source than a voltage source.

The exact physical mechanisms which result in enhancement of arc length for the first two of the above conditions are not known in detail. However, it is believed that the preferred symmetrical waveform enhances the formation of an electrical arc by reducing an effect known as "space charge screening" of the electric potential sources and by enhancing impact collisions between charged particles. Space charge screening occurs within a short time after initial free electron and ion formation. It is apparently caused by migration of free electrons and ions to the oppositely-charged potential sources. This migration produces a "space charge" of charged particles in the immediate vicinity of each source. Since the charged particles have a sign which is opposite to that of the adjacent electrode, the net effect is a reduction of the field gradient between the two potential sources. Therefore, the distance between the sources must be decreased in order to increase the field gradient to the point where the discharge becomes self-sustaining again. If, however, the sign of the electrical potential on each of the sources rapidly alternates, the space charge must continually migrate from one source to the other. This continual migration tends to break up the space charge formation and, in addition, as the mass of electrons and ions is swept through the electrode-tissue gap further ionization is enhanced by increased impact probability and the enhance of other physical processes. The net effect is an enhancement of the electrical discharge.

In order for the migration phenomenon to have its greatest effect on arc formation, it is necessary to have a large number of positive and negative cycles to maximize the probability of additional ionization. Consequently, the electric field should be maintained at a high value for as many cycles as possible—thus the reason for the second of the above-mentioned conditions. After arc formation, many cycles of the output waveform are necessary to maintain plasma formation between the output electrode and the tissue mass in order to provide an effective low impedance for maintaining the arc and enhancing arc length.

Figure 6A:
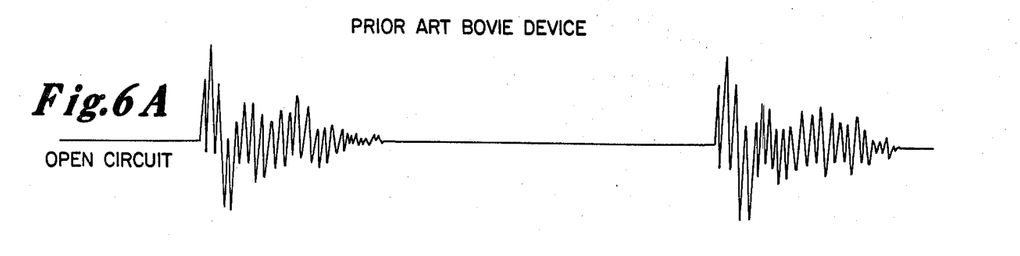
FIG. 6 discloses electrical output waveforms produced by prior art devices and the inventive fulguration circuitry.
Figure 6B:
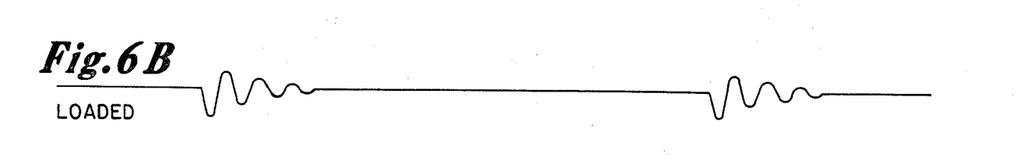
Figure 6C:
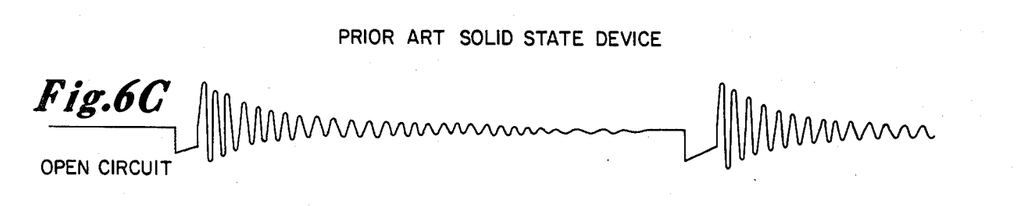
Figure 6D:
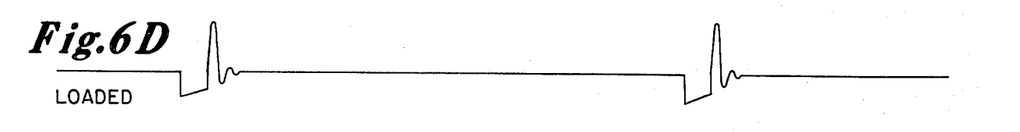
Figure 6E:
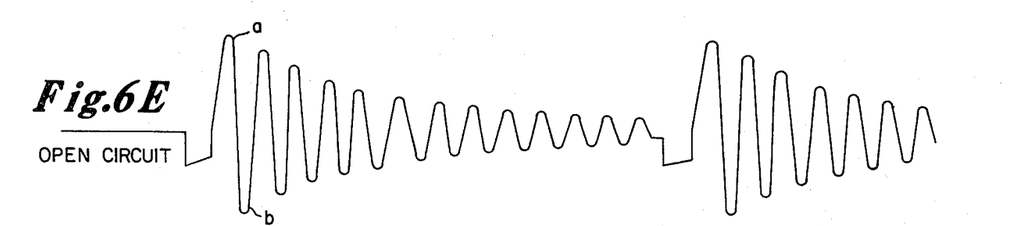

Taking into account the above conditions, one preferred "open circuit" fulguration waveform is shown in FIG. 6E. This waveform exhibits the desired symmetrical form and a low damping factor. In particular, peaks "a" and "b" are of similar shape and approximately the same amplitude. Due to the damping of the waveform, the amplitudes are not exactly the same, but because the damping factor is small they are substantially the same. Similarly, due to the small damping factor, each successive peak has substantially the same amplitude as the immediately previous peak.

Figure 6F:
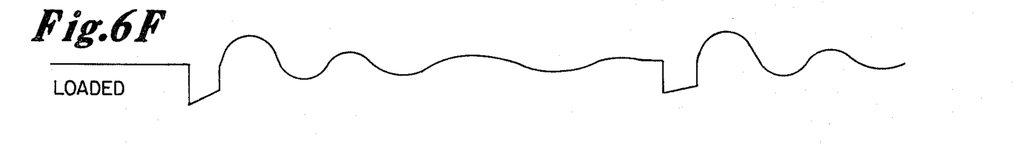

The "loaded" waveform shown in FIG. 6F is similar in appearance with symmetrical positive and negative peaks although greatly reduced in magnitude, of course. (In addition, in the actual waveforms produced by the illustrative embodiment of the invention, there is a reduction in frequency of about one-third due to the effect of leakage inductance which effects the output waveform only in the loaded condition).

Another preferred waveform is a constant amplitude sine wave signal or other periodic waveform of constant amplitude. This type of output can be produced with an oscillator circuit which is "driven" constantly and is normally used for cutting and dessication operations. However, if the generator internal impedance is increased in accordance with the invention, then a fulguration operation can be performed instead of cutting and or dessication operations.

Figure 1:
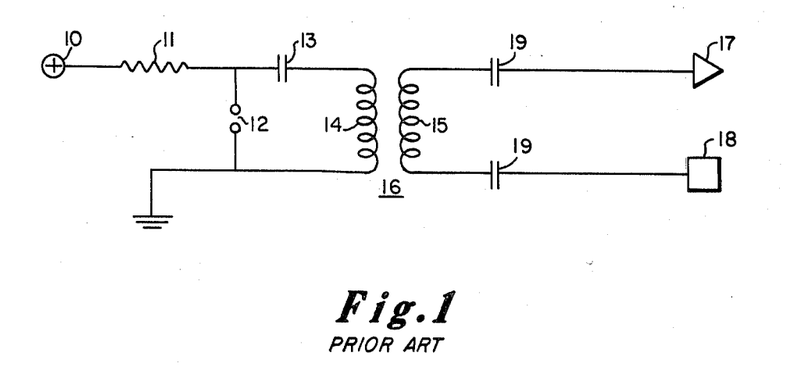
FIG. 1 shows a schematic diagram of the prior art "Bovie" apparatus.

Among prior art devices capable of producing fulguration effects is the prior art device known as a "Bovie" device. This device generates the necessary radio-frequency currents by means of a "spark-gap generator". A schematic diagram of the relevant circuitry is shown in FIG. 1. The circuitry uses a capacitor/inductor radio-frequency "tank" circuit with a spark-gap utilized as a high-frequency switch. In operation, capacitor 13 charges through resistor 11 from voltage source 10. When the voltage across capacitor 13 reaches the breakdown voltage of spark-gap 12, an electrical arc forms across gap 12, effectively creating a low impedance and connecting capacitor 13 in parallel with primary winding 14 of output transformer 16. The secondary winding 15 of transformer 16 is connected to the output electrodes consisting of active electrode 17 and patient, or return, plate 18. Capacitors 19 prevent harmful low-frequency currents from flowing in the secondary circuit.

When an electrical arc occurs across spark-gap 12, the circuit begins oscillations at a characteristic frequency determined by the values of capacitor 13 and the inductance of transformer primary winding 14. The oscillation amplitudes start at a peak voltage determined by the values of the circuit components and decrease exponentially at a rate which is determined by the value of capacitor 13, the amount of resistance in the circuit and the amount of loss in transformer 16. The circuit resistance consists of the sum of the resistance of winding 14 and the value of the load impedance at electrodes 17 and 18 which "reflected" back through secondary winding 15 of transformer 16. In actual operation, before a fulguration arc occurs from active electrode 17 to the tissue mass, the impedance across the electrodes 17 and 18 is relatively high. Thus, the decay of the oscillations in the radio-frequency tank circuit are determined mainly by the resistance of primary winding 14 and the amount of loss in transformer 16 and the characteristics of the spark gap.

In the typical "Bovie" circuit, the selection and arrangement of the components produce an output waveform in the "open circuit" condition which contains a significant amount of higher-order harmonics. This characteristic produces the unsymmetrical waveform shown in FIG. 6A. Because of the higher-order harmonics present, the waveform is no longer symmetrical around zero during each of its periods. Thus, the first condition for a preferred waveform discussed above is not met and as a result the active electrode must be brought close to the tissue surface before an arc forms. Also, in a typical prior art "Bovie" circuit, the components are intentionally chosen so that in an "open circuit" condition (prior to arc formation) the oscillation waveform is highly damped as shown in FIG. 6A. Apparently, it was believed that a high damping factor was necessary (alternatively, that the waveform have a high "crest factor", defined as the ratio of peak value of voltage or current to RMS value of voltage or current) so that the overall waveform had a low duty cycle in order to minimize cutting effects during the fulguration operation. Unfortunately, no distinction was made in the prior art between waveform shapes before and after arc formation and thus the circuit was optimized to produce the best waveform (or a waveform with a high "crest factor") after arc formation. Thus the second condition for a preferred waveform is also not met.

After arc formation, the low load impedance is reflected through the output transformer into the oscillator circuit so that the waveform is more nearly symmetric during each of its cycles. The reduced load impedance also causes an increase in the damping as shown in FIG. 6B. Unfortunately, because of the high initial damping factor, the waveform becomes attenuated so rapidly due to the decreased load impedance that the arc length produced by this device is very short.

In accordance with the teachings of this invention, the output of the prior art "Bovie" device can, in fact, be improved by placing a relatively low resistance (on the order of 500 ohms) across the output so that the "open circuit" waveform is similar to the waveform shown in FIG. 6D. If this is done, even though the damping factor is quite high and the second condition for a preferred waveform is not met, the waveform exhibits the proper positive and negative symmetry and thus the device initiates the arc sooner than it would if the circuit was unloaded. Thus the modification results in a significant increase in arc length for a given peak voltage and improves performance of the unit.

In addition to the prior art "Bovie" type circuits various solid state circuits have been used in the prior art. Most of these circuits have tended to imitate the "Bovie" output waveform in an attempt to copy the performance of the unit. In many of these circuits the higher order harmonics present in the Bovie circuit in the "open circuit" condition has been eliminated resulting in the proper symmetrical waveform. However, typically in these units, the damping factor is very high in an attempt to achieve a high "crest factor" and thus minimize cutting effects. The high damping factor effectively produces asymmetry in the waveform during each cycle as shown in FIG. 6C. Thus, the conditions stated above are not met and the active electrode must be moved very close to the tissue mass before arc formation occurs. After arc formation, attenuation of the waveform is increased even more, resulting in the loaded waveform as shown in FIG. 6D. This waveform is even more asymmetrical consisting of a very large positive pulse with only an almost imperceptible negative pulse.

Figure 2:
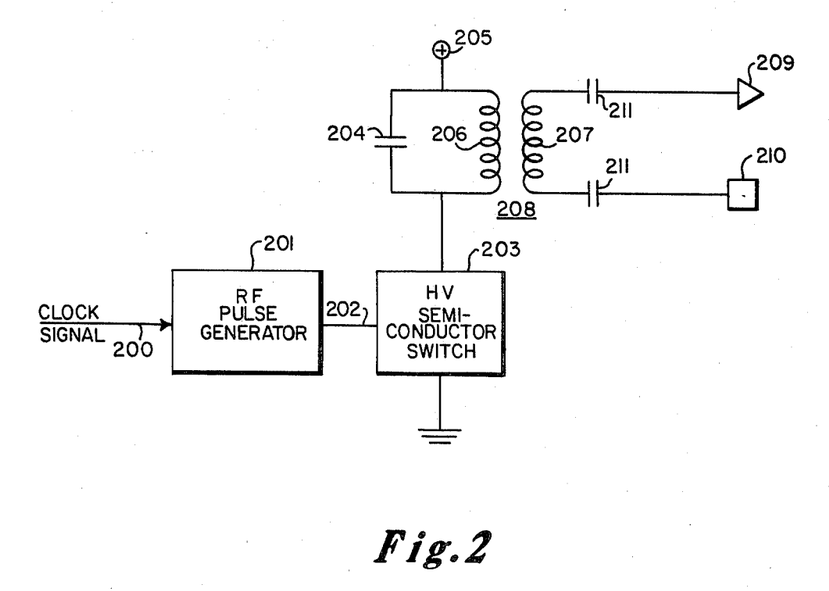
FIG. 2 is a block schematic diagram of the inventive fulguration circuitry.

The preferred waveform shown in FIGS. 6E and 6F can be produced in accordance with the principles of this invention by the circuitry shown in block diagram in FIG. 2. In this circuit radio-frequency oscillations are produced by means of a high "Q" oscillator circuit in which the output impedance has been increased by choosing a small value of capacitance and increasing the secondary/primary turns ratio of the output transformer. Specifically, radio-frequency oscillations are produced by the "tank" circuit consisting of capacitor 204 and the primary winding 206 of output transformer 208. In operation, the tank circuit is connected to a source of high D.C. voltage 205 by means of semiconductor switch 203. Source 205 may illustratively be a regulated D.C. supply which produces a D.C. voltage of between 0 and 200 volts D.C. Any regulated supply may be used. For example, a supply which is suitable for use with the illustrative embodiment is a Sorensen Model DCR 600-3B. The power supply may be controlled from controls on the control panel of the electrosurgical generator or may be controlled by a feedback network to provide constant power under varying load conditions. A feedback network suitable for use with the illustrative embodiment is disclosed in U.S. Pat. No. 3,601,126 issued on Aug. 24, 1971 to J. R. Estes.

Semiconductor switch 203 is, in turn, controlled by control circuit 201 via lead 202. Control circuit 201 produces control pulses in response to a clock signal on lead 200, which signal synchronizes the operation of the entire circuitry. In order to produce a high-frequency output, the semiconductor switches are closed and opened under control of control circuit 201. This operation periodically connects the tank circuit to ground permitting current to flow from power source 205 through primary winding 206 of transformer 208 and semiconductor switch 203.

After a controlled interval of time, switch 203 is opened causing the tank circuit (consisting of capacitor 204 and inductor 206) to begin "ringing" at a characteristic frequency determined by the capacitor and the inductor values. The frequency of oscillation is illustratively chosen to be 500 kilohertz. This frequency is high enough to prevent neuromuscular stimulation (which may be dangerous to the patient) yet low enough to prevent a deep necrosis from being produced by the radio-frequency energy. The waveform open-circuit produced by this circuit has the mathematical function with respect to time, t, of $e^{-\zeta\omega_n t} \sin(\omega_n\sqrt{1-\zeta^2}t+\phi)$, where $\omega_n$ is the undamped, natural frequency of oscillation and $\zeta$, the damping ratio, determines the rate of decrease in the sine wave amplitude. It has been found that to produce a satisfactory fulguration waveform $\zeta$ must be less than or equal to 0.038. Specifically, in the first illustrative embodiment, $\zeta$ is equal to 0.025 and in the second $\zeta$ is equal to 0.038.

After an electrical arc has been established between the output electrodes and the tissue mass, the relatively low load impedance of the tissue mass at the output electrodes is "reflected" back through the secondary winding 207 of transformer 208 to the primary winding 206 as a low impedance which "loads" the the tank circuit consisting of capacitor 204 and inductor 206. When the tank circuit is so loaded, the loaded output waveform shape remains of the form $$e^{-\zeta\omega_n t} \sin(\omega_n\sqrt{1-\zeta^2}t+\phi),$$

but the damping factor $\zeta$ of the loaded tank circuit increases to a value substantially greater than 0.038.

The output power of the device may be varied by varying either the D.C. supply voltage or by varying the amount of time the semiconductor switches are closed. Either method varies the initial amount of peak current flowing in the transformer primary winding and thus the output power. The signal produced by the tank circuit is coupled to secondary winding 207 of transformer 208 and thence, via capacitors 211, to the active electrode 209 and patient plate 210.

In accordance with the principles of the invention, the preferred "open circuit" (prior to arc formation) waveform shown in FIG. 6E is produced by the characteristics of the tank circuit and transformer 208. In particular, the "open circuit" damping factor of the circuit, which is inversely proportional to the "Q" factor of the circuit, is related to the resistance of primary winding 206 and the flux leakage in transformer 208. In order to increase the "Q" of the circuit, transformer 208 is specially designed to reduce internal losses and "corona breakdown", thus reducing the damping factor as much as possible and allowing the oscillations to continue for a much longer period during the open circuit condition.

Specifically, transformer 208 is constructed on a powered-iron carbonyl-C toroidal core instead of an air core or ferrite air-gapped core. A suitable core which may be used in the illustrative embodiment is a model FE 2500-0101 manufactured by Arnold Engineering, Inc. This core is insulated with a layer of insulating tape (illustratively #10 tape manufactured by the 3M Company, with 50% overlap). The secondary winding is then added, consisting of 75 turns, single layer progressive wind of #26 magnet wire. The primary winding, consisting of 13 turns of 30 Kv high voltage silicon rubber wire (Markel #4155-22-300730), is added. Finally, the entire transformer is vacuum-impregnated with varnish and encapsulated in epoxy.

In addition, the component values are chosen to give a high output impedance to limit arc current. Specifically, capacitor 204 illustratively has a value of 4.5-5.5 nanofarads. Similarly, as discussed above the turns ratio of the transformer 208 is 1:5.77. The values give a "Q" of 20 and an output impedance of 1245 ohms at a fundamental frequency of 500 kilohertz. The output impedance can be increased as desired by in turn increasing the primary/secondary turns ratio by increasing the number of a secondary turns.

The above values produce a circuit which is suitable for general use. It has been found that an output impedance of at least 1000 ohms at the fundamental frequency of oscillation is necessary to avoid significant cutting and burning effects. In some cases, however, especially when needle electrodes are used it is useful to have a higher open-circuit output voltage and a higher generator output impedance in order to limit heating of the electrode tip. For these cases, the transformer may be constructed with the same materials but the number of secondary turns increased to 133 and the number of primary turns to 14, giving a primary/secondary turns ratio of 1:9.5. In order to to maintain a resonant frequency of 500 kilohertz, capacitor 204 must have a corresponding value of 2-3 nanofarads. With these values the "Q" of the circuit is approximately 13 and the output impedance at 500 kilohertz is 2789 ohms.

Figure 3:
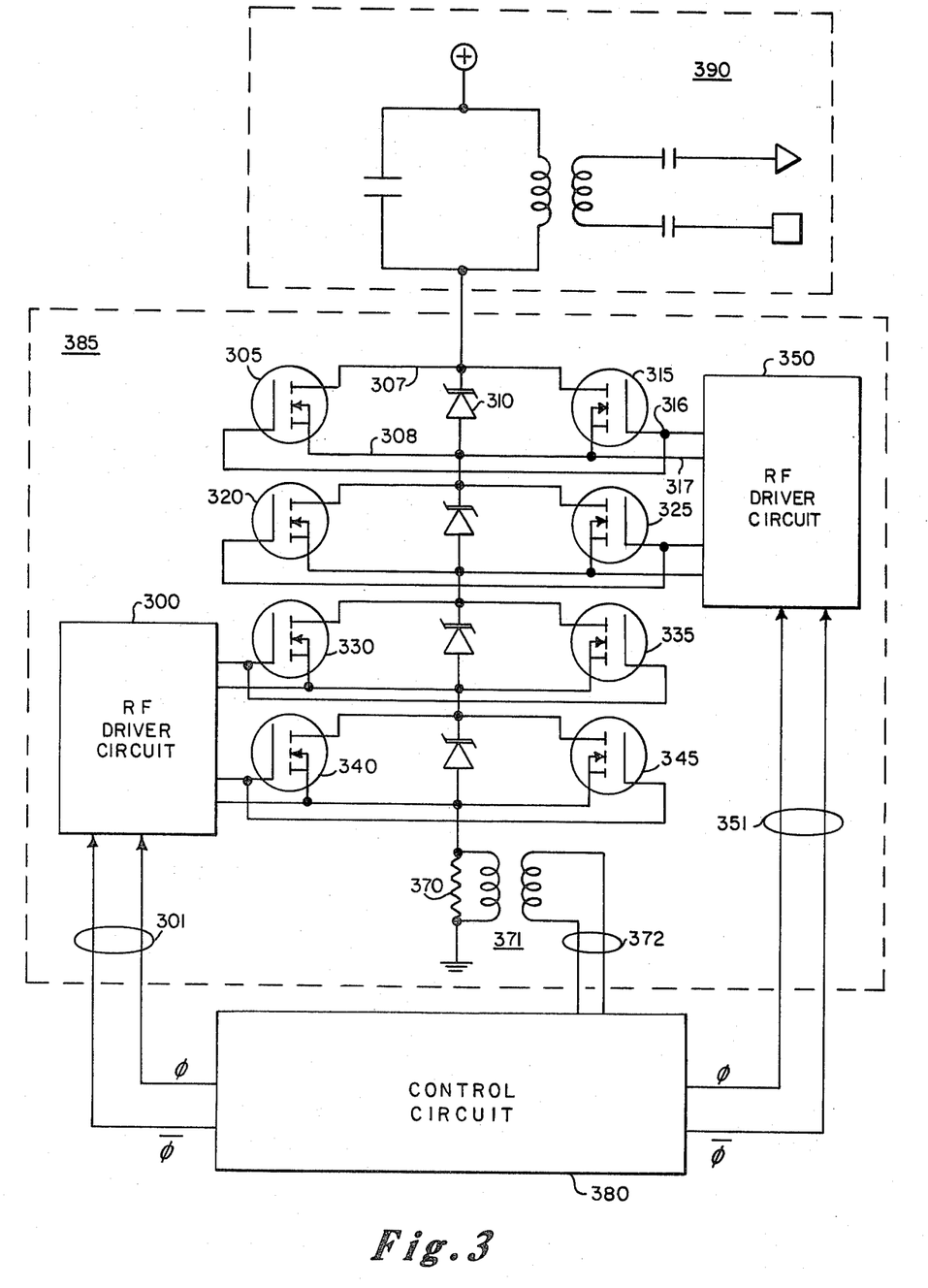
FIG. 3 is an expanded schematic diagram of the apparatus shown in FIG. 2.

FIG. 3 of the drawing illustrates in greater detail the circuitry shown in the block schematic diagram of FIG. 2. In particular, the construction of the high voltage semiconductor switch is shown in detail. Referring to FIG. 3, the output tank circuitry and the output electrodes are shown in dotted box 390. The semiconductor switch is shown in dotted box 385 and the control circuit is shown in box 380.

High voltage switch 385 is comprised of four identical semiconductor switches connected in series configuration in order to prevent electrical breakdown of the semiconductor devices due to the high voltages involved in the tank circuit oscillations. Two of the four semiconductor switches are controlled by each of R.F. driver circuits 300 and 350. Driver circuits 300 and 350 are, in turn, controlled by control circuit 380 by means of leads 301 and 351 respectively. Each semiconductor switch consists of two VMOS semiconductive switches connected in parallel in order to handle the high current involved. For example, VMOS switches 305 and 315 comprise one semiconductor switch. A semiconductor device which is suitable for use in the illustrative circuit is the device number MTM565 manufactured by Motorola Semiconductor Products, Ponenix, Ariz. The drain electrodes of devices 305 and 315 are connected together and to the radio-frequency tank circuit by means of lead 307. Similarly, the source electrodes are connected together by means of lead 308. Connected across the source and drain of both devices is a high-voltage diode 310 which is used as a transient absorber that breaks down upon the occurence of a high voltage spike and prevents devices 305 and 315 from being destroyed by a secondary breakdown. A suitable protection device for use with the illustrative embodiment is the device number 1.5 KE 250 "Transorb" manufactured by General Semiconductor. The gate electrodes of devices 305 and 315 are connected together and to R.F. driver circuit 350 by means of lead 316. Similarly, the source leads are connected by means of lead 317 to R.F. driver circuit 350. As will be hereinafter described, driver circuit 350 controls devices 305 and 315 by placing voltages on leads 316 and 317. Specifically, when lead 316 is positive with respect to lead 317, devices 305 and 350 turn on and conduct current via leads 307 and 308 through the switch.

Similarly, three other semiconductor switches consisting of device pairs 320, 325; 330,335 and 340, 345 are connected in series. As will be hereinafter described, driver circuits 350 and 300 control all switches to turn them "on" and "off" simultaneously. Current thus flows in a controlled manner through the devices and resistor 370 to ground.

As described hereinafter, resistor 370 is a low value (approximately 0.1 ohms) resistor used to sense the current flowing through the switches to prevent them from being overloaded. The voltage developed across the resistor 370 (which is proportional to the current running through the semiconductor switches) is coupled by transformer 371 and lead 372 to control circuit 380 and responsive thereto, as the current increases, control circuit 380 reduces the "on" time of the semiconductor switches thereby reducing the current and preventing damaged switches.

Figure 4:
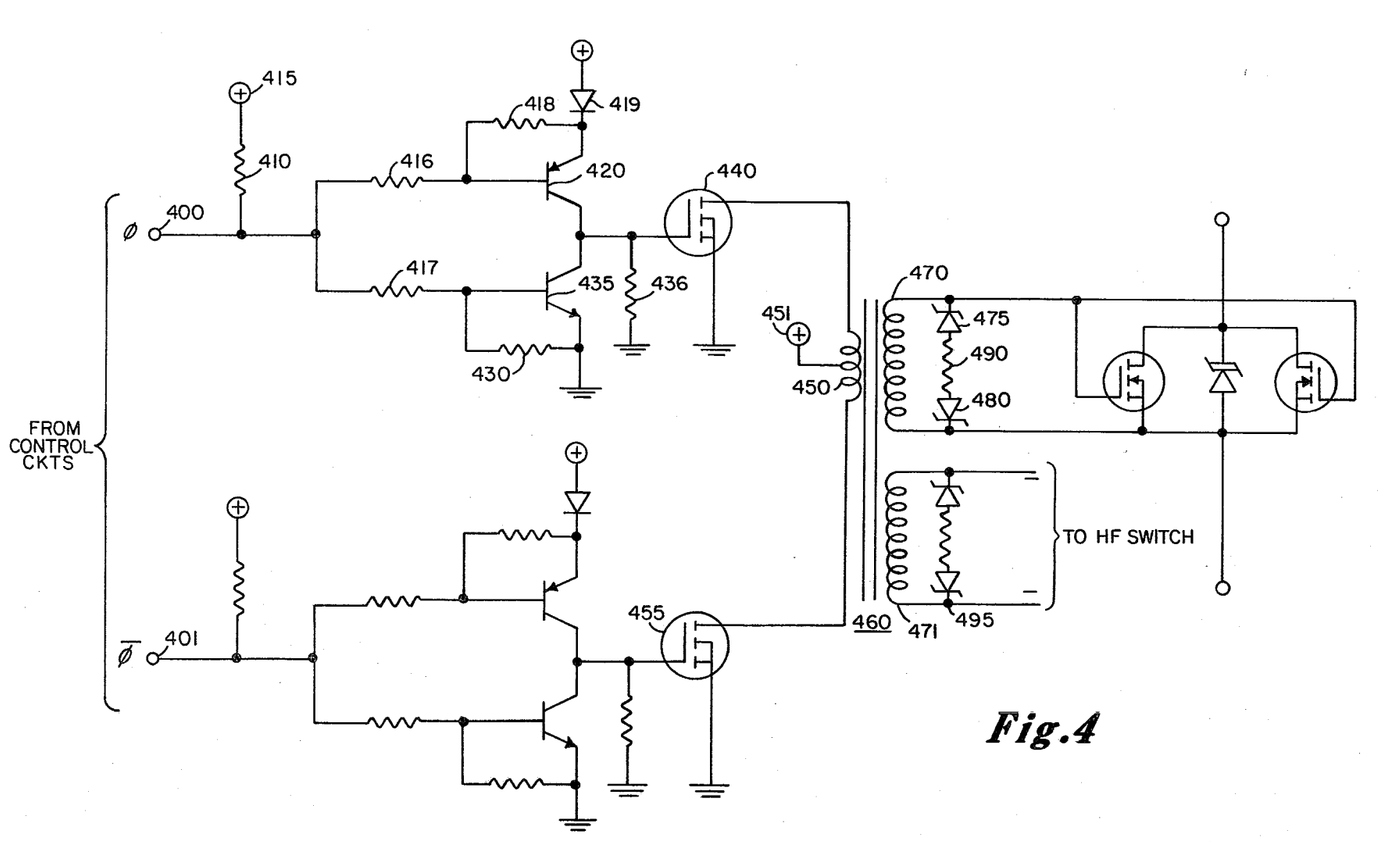
FIG. 4 is a schematic diagram of the radio-frequency driver circuitry.

FIG. 4 shows the circuitry of the R.F. driver units 300 and 350 shown in block fashion in FIG. 3. Each of driver circuits 300 and 350 is identical to the circuit shown in FIG. 4. The driver circuits are controlled by the signals φ and 100 provided from the control circuit via terminals 400 and 401 shown at the left side of the Figure. The driver unit itself consists of two semiconductor switch units which are identical. Since the switch units are identical only one will be described.

Each of the switch units is connected to one end of a center-tapped primary winding 450 of transformer 460. The secondary of transformer 460 drives the semiconductor high voltage switches. In the quiescent or "off" state, input 400 of the upper unit is normally held at a "high" voltage by means of the output gate circuitry of the timing circuit (resistor 40 which is connected to positive voltage source 415 also helps to keep input 400 in a "high" state). The positive voltage on terminal 400 is applied via the resistive divider, consisting of resistors 417 and 430, to the base of transistor 435, turning it "on". In its "on" state, transistor 435 places a low signal (near ground) on its collector. The gate electrode of FET switch 440, which is connected to the collector of transistor 435, is thus held at ground and FET 440 is therefore held "off". In addition, the high signal appearing on terminal 400 is applied via the resistive divider, consisting of resistors 416 and 418, to the base of transistor 420 holding it in its "off" state.

The driver unit becomes active when the control circuitry places a negative-going pulse on terminal 400. The negative-going pulse is applied, via the resistive divider consisting of resistors 417 and 430, to the base of transistor 435, turning it off. In addition, the negative-going pulse is applied via the resistive divider, consisting of resistors 416 and 418, to the base of transistor 420, turning it on. Current thus flows through diode 419 and transistor 420 and resistor 436 to ground, raising the potential on the gate lead of FET switch 440. In response thereto, FET switch 440 turns on and current flows from positive voltage source 451 through one half of the primary windings 450 of transformer 460 through FET switch 440 to ground. Transformer 460, in turn, controls the high voltage switches by means of two secondary windings 470 and 471 (in the diagram, for clarity, only winding 470 is shown connected to a high voltage switch. Secondary winding 471 is connected in an analogous manner to another switch). The output of winding 470 is connected to the gate and drain electrodes of the high voltage FET switches. In addition, a pair of Zener diodes 475, 480 (having a breakdown voltage rating of approximately 12 volts) in series with resistor 490 are connected across winding 470. These three components prevent an accidental high voltage spike occurring across secondary 470 from damaging the high voltage FET transistors.

At the end of the "on" time interval, the voltage on terminal 400 again returns to its quiescent high state. Terminal 400 is then pulled high by means of resistor 410; transistor 435 turns "on" and transistor 420 turns "off", thereby allowing resistor 436 to return the potential on the gate electrode of FET 440 to ground. Responsive thereto, FET 440 ceases conducting and current ceases flowing from source 451 through the primary winding 450 of transformer 460.

However, in order to insure quick turnoff of the high voltage switches, the current in the primary winding 450 of transformer 460 is effectively "reversed" to "dump" the flux in the transformer windings insuring that the voltage in the secondary falls quickly to zero. In particular, as hereinafter described, a short time after terminal 400 returns to its quiescent high state the control circuitry places a short negative-going pulse of approximately 200 nanoseconds in duration on terminal 401. In a manner analogously described to the upper switch circuit, the lower switch circuit in the R.F.

driver turns "on" FET 455, causing current to flow from source 451 through the primary winding 450 of transformer 460. This current will be flowing in a direction opposite to the immediately previous current flow. The magnetic flux resulting in the transformer core is in a direction opposite to that produced by the negative-going pulse on terminal 400. Any residual flux in the core will thus be "cancelled" insuring quick turnoff of the high voltage switches.

Figure 5:
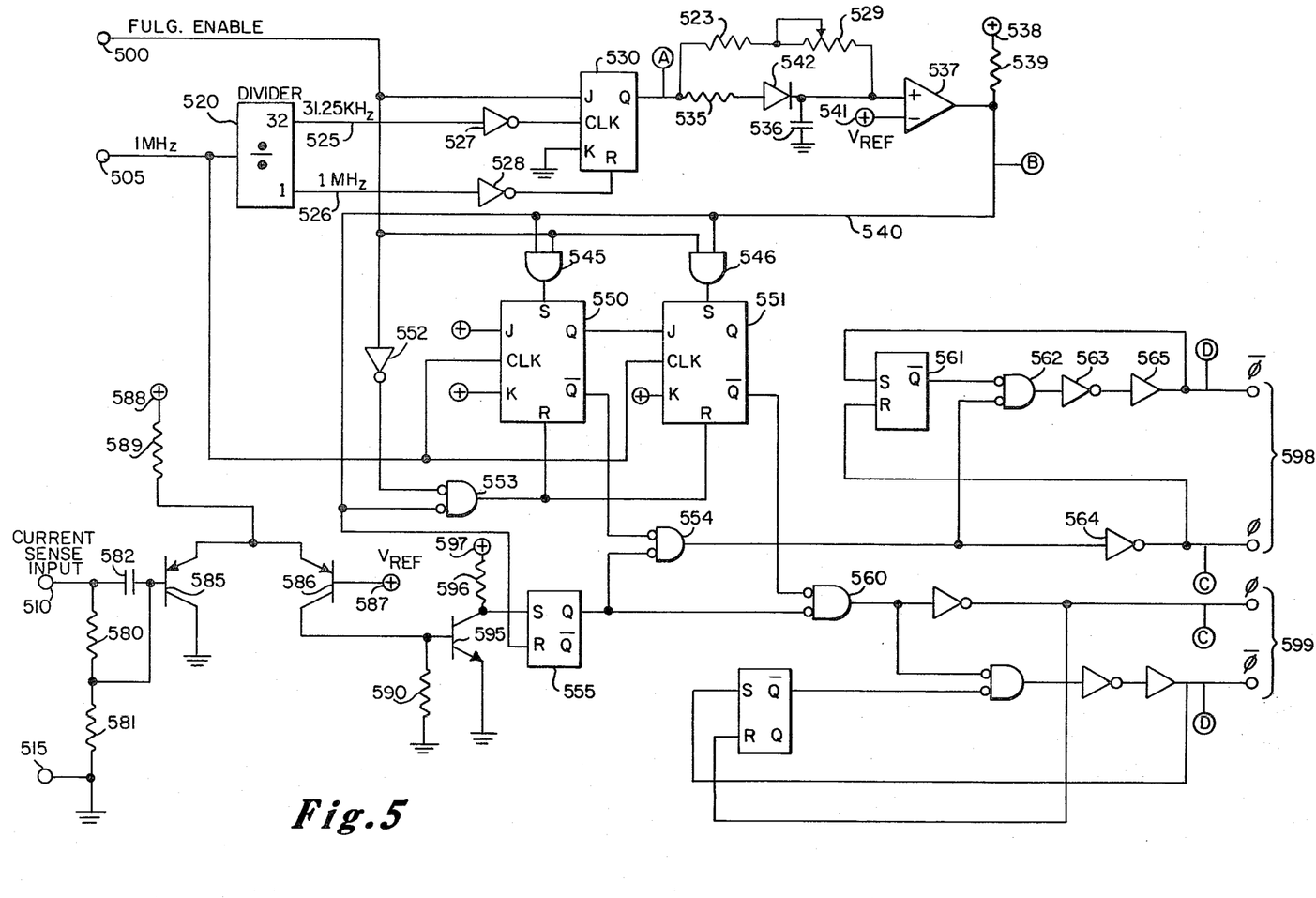
FIG. 5 is a schematic diagram of the control circuitry.

The control circuitry which produces the timing pulses that in turn control the R.F. driver circuits and the high voltage switches is shown in FIG. 5. The circuitry has four inputs as shown on the lefthand side of the Figure. The first input is FULGURATION ENABLE lead 500. A logical "high" signal on this lead enables the control circuitry to produce timing signals which operate the R.F. circuitry to produce a fulguration output. Alternatively, a logical "low" signal on this lead disables the timing circuitry and thus no fulguration output is produced.

The control circuitry also receives a one megahertz clock signal on terminal 505. This signal is a simple one megahertz squarewave signal which may be generated by standard, well-known clock circuitry which will not be discussed further herein.

The final two inputs to the control circuitry are the current-sense inputs 510 and 515 which are connected to leads 372 in FIG. 3 and receive a voltage which is proportional to the current running through the high voltage switches. As will be hereinafter described, the voltage appearing across terminals 510 and 515 is used by the control circuit to control the pulse width of the signal pulses and thereby to control the current through the high voltage switches.

The one megahertz clock signal input on terminal 505 is provided to the input of divider 520. Divider 520 is a digital circuit which produces output pulse trains at a fraction of the frequency of the input pulse train. Such divider circuits are well-known in the art and will not be described further hereinafter. Divider 520 has two outputs 525 and 526. The waveform appearing on output 525 is a squarewave pulse train at a frequency of 31.25 kilohertz or 1/32 of the frequency of the one megahertz input waveform. The waveform appearing on output 526 is a squarewave pulse train at a frequency of 1 megahertz or equal to the frequency of the input waveform. Output 525 of the divider 520 is inverted by invertor 527 and applied to the clock input of J-K flip/flop 530. Similarly, output 526 of divider 520 is inverted by invertor 528 and applied to the reset input of J-K flip/flop 530. Flip/flop 530 is a well-known circuit device which provides a "high" signal on its Q output on the falling edge of a clock pulse if a "high" signal is provided to its J input and a "low" signal is provided to its K input.

Figure 7:
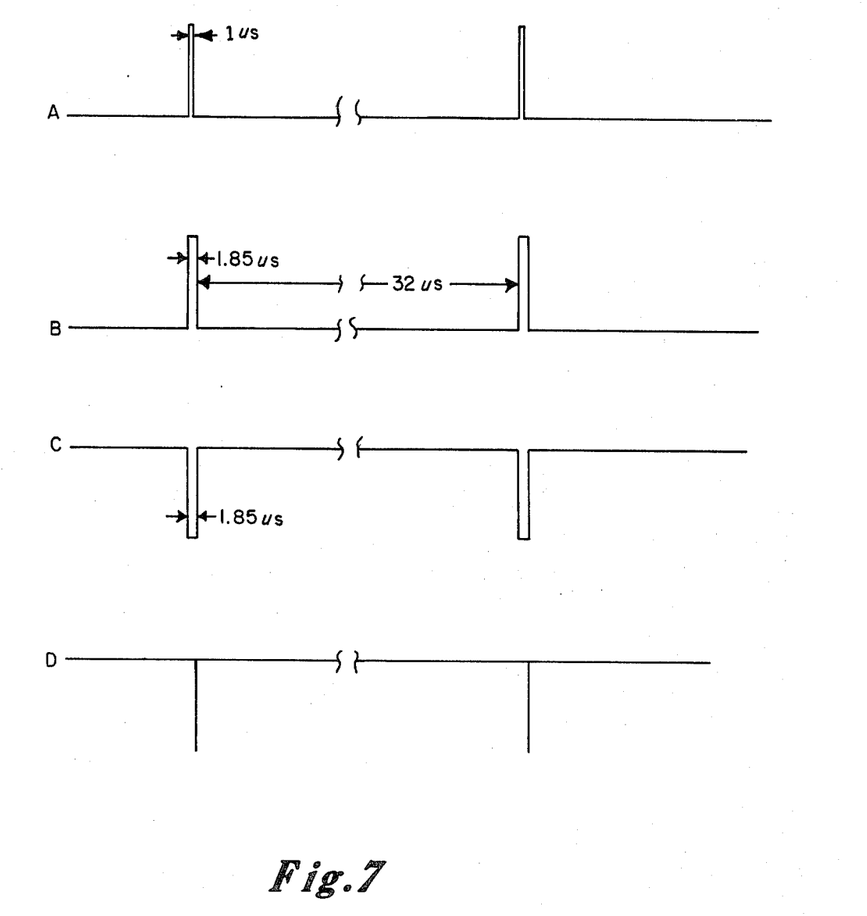
FIG. 7 discloses electrical waveforms produced internally by the circuit shown in FIG. 5.

Assuming the control circuitry is conditioned to provide output signals by a "high" signal on the FULGURATION ENABLE lead 500, a "high" signal is provided to the J input of flip/flop 530 by means of lead 500. Therefore, in response to the signals provided to its clock input and reset input, J-K flip/flop 530 provides on its Q output a signal which consists of a train of pulses one microsecond in duration at a 31.25 kilohertz repetition rate. In particular, flip/flop 530 provides a high signal on its Q output on the falling edge of every clock pulse provided to its clock input from divider 520. The flip/flop is reset to remove the high signal from the Q output in response to the 1 megahertz signal provided to its reset input. The output of flip/flop 530 is therefore the signal shown in FIG. 7, line A.

This signal is provided to the pulse-width determining circuitry consisting of the resistors 523, 529 and 535, diode 542, capacitor 536 and comparator 537. In particular, the high signal at the output of flip/flop 530 charges capacitor 536 via resistor 535 and diode 542. Resistor 535 is a low value so capacitor 536 charges quickly. The increasing voltage on capacitor 536 is compared to a reference voltage source 541 by comparator 537. When the voltages are equal, comparator 537 provides a "high" signal output and line 540 is pulled "high" by resistor 539 and voltage source 538. When the output of flip/flop 530 becomes low at the end of each one microsecond pulse, capacitor 536 begins discharging through variable resistor 529 and resistor 523. Diode 542 prevents capacitor 536 from discharging through resistor 535. Resistor 529 and 523 are of much higher value than the value of resistor 535 and thus the discharge time of capacitor 536 is much longer than its charging time. The pulse-width determining circuitry therefore acts as a pulse "stretcher" and the time at which the voltages at the inputs of comparator 537 become equal is determined by the adjustment of resistor 529. Similarly, the width of the pulses present at the comparator output 540 is dependent on the adjustment of variable resistor 529. In the illustrative embodiment, variable resistor 529 is adjusted so that the width of the pulses produced on the output of comparator 537 is approximately 1.85 microseconds as shown in line B of FIG. 7 (for the second embodiment the pulse width is adjusted to be 2.3 microseconds).

The pulses on lead 540 are connected to one input of AND gates 545 and 546. The other input of gates 545 and 546 is enabled by the high signal on the FULGURATION ENABLE lead 500. Thus, gates 545 and 546 deliver a high pulse to the set inputs of J-K flip/flops 550 and 551 at a 31.25 kilohertz repetition rate. the signal on lead 540 is also applied to one input of AND gate 553. AND gate 553 also receives a "low" input from the output of invertor 552 which receives the FULGURATION ENABLE lead 500 at its input. Gate 553 produces a high signal only when both of its inputs are low and this low signal is applied to the reset input of flip/flops 550 and 551. Thus, flip/flops 550 and 551 receive set signals when the signal on lead 540 is high and reset signals when it is low. Flip/flops 550 and 551 therefore act as latches and produce an output signal which is similar to line B in FIG. 7 although slightly delayed in time. This is true even though clock signals are provided from lead 505 to the clock inputs of flip/flops 550 and 551, since, as is well-known in the art, the set and reset inputs override the clock inputs and signals present on the J-K inputs. Signals appearing on the $\overline{Q}$ outputs of flip/flops 550 and 551 are provided to gates 554 and 560 respectively. As will be hereinafter described, gates 554 and 560 control the width of the control circuit output pulses based on the current input sensed on inputs 510 and 515.

Assume for the moment that the output of set-reset flip/flop 555 is low. Thus, both gates 554 and 560 are enabled. Enabled gates 554 and 560 provide input signals to the output signal generation circuitry which generates a pair of $\phi$ and $\overline{\phi}$ driving signals on leads 598 and 599 respectively. The output circuitry is duplicated for each set of outputs and thus only the upper arrangement will be described in detail; the lower one operating in an analogous fashion.

Specifically, the pulses produced at the $\overline{Q}$ output of flip/flop 550 pass through enabled gate 554 and are inverted by invertor 564 to appear on the $\phi$ output of terminals 598. These signals appear as an inversion of the 1.85 microsecond pulses produced on the output of comparator 537 as shown in line C of FIG. 7. As previously described, the pulses are applied to the R.F. driver circuitry enabling the high frequency switches which, in turn, drive the R.F. tank circuits to produce an output voltage. In addition, the "high" signal to the output of gate 554 is supplied to the input of gate 562 to disable it. In response, gate 562 places a "low" signal on its output which is applied to the input of invertor 563 which, in turn, places a "high" signal on its output. The "high" signal at the output of invertor 563, in turn, is applied to the $\overline{\phi}$ output by buffer gate 565. At this time, the "high" signal at the $\overline{\phi}$ output is applied to the set input of set-reset flip/flop 561, setting it to produce a "low" signal at its Q output which signal is applied to the upper input of gate 562, partially enabling it.

At the end of the output on the $\phi$ output, the signal on the $\overline{Q}$ output of flip/flop 550 becomes "high" disabling gate 554 and causing it to place a "low" signal on its output. This "low" signal is inverted by invertor 564 and appears as a "high" signal on the $\phi$ output which in turn turns "off" the R.F. drivers as previously described. The "low" signal on the output of gate 554 is also applied to the lower input of gate 562, fully enabling it and causing it to produce a "high" signal on its output which signal is inverted by invertor 563 and passes through buffer amplifier 565 as a "low" signal to the output $\overline{\phi}$. As previously described, this signal is used to "dump" the flux in the driver transformer of the associated R.F. driver circuitry.

The "low" signal on the output $\overline{\phi}$ is also applied to the set input of set-reset flip/flop 561, setting the flip/flop which, in turn, produces a "high" on its output $\overline{Q}$ which signal, in turn, disables gate 562. Disabled gate 562 produces a "low" signal output which low signal is inverted by invertor 563 and applied to buffer amplifier 565. Amplifier 565 produces a "high" signal on the $\overline{\phi}$ output of terminals 598. The signal on the $\overline{\phi}$ output is therefore "low" only for a short period of time which is equal to the cumulative propagation delays of set-reset flip/flop 561 and gates 562, 563, and 565. The cumulative delay totals approximately 200 nanoseconds. The 200-nanosecond pulse produced on the $\overline{\phi}$ output, as described above, is used to "dump" the flux from the transformer of the associated radio frequency driver circuit to insure quick turnoff of the high voltage switching circuits.

The $\phi$ and $\overline{\phi}$ outputs associated with output terminals 599 operate in an exactly similar way driven by the output signal provided by gate 560.

In order to prevent damage to the high voltage switching circuitry, gates 554 and 560 are controlled by the current limiting circuitry consisting of transistors 585, 586, and 595 and set-reset flip/flop 555. Specifically, as the current flowing through the high voltage switching circuitry increases, set-reset flip/flop 555 becomes set during the output signal pulse produced by the control circuitry and disables gates 554 and 560, turning "off" the output signal before "turnoff" would normally occur. In particular, as previously described, as the current through the high voltage switching circuitry increases, potential drop across the current-sense input terminals 510 and 515 increases. This potential is impressed across the resistive divider consisting of resistors 580 and 581. An increasing potential at the junction of resistors 580 and 581 is applied to the base of transistor 585. Capacitor 582 is used to speed up the response-time of transistor 585. Transistor 585 together with transistor 586 comprise a differential amplifier. According to well-known principals of differential amplifiers, as transistor 585 turns "off" in response to the increasing potential at the junction of resistors 580 and 581, transistor 586 becomes more "turned-on". Specifically, as transistor 585 turns "off", less current is drawn therethrough and the current running through resistor 589 from voltage source 588 decreases. Thus, the potential at the emitter of transistor 586 increases. Since the base of transistor 586 is connected to the voltage reference source 587, transistor 586 tends to be "turned-on" and increases its current flow. An increased current flow from the collector of transistor 586 is applied to resistor 590 and the base of transistor 595, tending to turn it "on". As transistor 595 turns "on" the current through it increases, thereby increasing the voltage drop across resistor 596. Therefore, with increasing current the signal applied to the set input of set-reset flip/flop 555 decreases.

At some point, flip/flop 555 is set and its Q output becomes "high", disabling gates 554 and 560. Thus, as the current through the high voltage switching circuitry increases gates 554 and 560 are turned off earlier and earlier during the "on" cycle, reducing the effective pulse width of the control circuit output signal and the current flowing through the high voltage circuitry. At the end of the pulse, a "low" signal provided via lead 540 to the reset input of set-reset flip/flop 555 resets the flip/flop for another cycle.

Although specific circuitry is shown in the illustrative embodiment, there will be many variations of the illustrative embodment which will be immediately apparent to those skilled in the art and which embody the spirit of the invention. For example, a different radio-frequency oscillator may be substituted for the radio-frequency tank circuit of the illustrative embodiment with the characteristics of the oscillator circuit adjusted to produce the preferred waveform.

What is claimed is:

1. An electrosurgical generator for performing surgical operations on a tissue mass comprising:
    an active electrode,
    a return electrode,
    means for generating a damped oscillatory open circuit output voltage waveform across said electrodes, said waveform being substantially of the form $e^{-\zeta\omega_n t} \sin(\omega_n\sqrt{1-\zeta^2}t+\phi)$, where e is the base of the natural logarithm, $\omega_n$ is the undamped, natural frequency, $\zeta$ is the damping factor and is equal to or less than 0.038, but greater than 0 and $\phi$ is a phase angle, said generating means generating a loaded output voltage waveform across said electrodes after an electrical arc forms between said tissue mass and said active electrode, said loaded waveform being substantially of the form $e^{-\zeta\omega_n t}\sin(\omega_n\sqrt{1-\zeta^2}t+\phi)$, where e is the base of the natural logarithm, $\omega_n$ is the undamped, natural frequency, $\zeta$ is the damping factor and is substantially greater than 0.038.

2. An electrosurgical generator according to claim 1, wherein the open circuit damping factor $\zeta$ is substantially equal to 0.038.

3. An electrosurgical generator according to claim 1, where the open circuit damping factor $\zeta$ is substantially equal to 0.025.

4. An electrosurgical generator according to claim 1, wherein said generating means has sufficient internal impedance to prevent electrosurgical cutting from occurring.

5. An electrosurgical generator according to claim 4, wherein said internal impedance is substantially equal to or greater than 1000 ohms at the fundamental frequency of operation.

6. An electrosurgical generator according to claim 4, wherein said internal impedance is substantially equal to or greater than 1000 ohms at a fundamental frequency of 500 kilohertz.

7. An electrosurgical generator for performing fulguration on a tissue mass, said generator comprising,
an electrical tank circuit comprising a capacitor and a transformer having a primary and a secondary winding, said capacitor being connected in parallel with said primary winding,
means for repetitively exciting said tank circuit at a repetition rate substantially lower than the resonant frequency of said tank circuit to generate an open circuit damped voltage waveform having substantially the form $$e^{-\zeta\omega_n t}\sin(\omega_n\sqrt{1-\zeta^2}t+\phi),$$

where e is the base of the natural logarithm, $\omega_n$ is the undamped, natural frequency, $\zeta$ is the damping factor and is equal to or less than 0.038, but greater than 0 and $\phi$ is a phase angle, and
means connected to said secondary winding for applying the output signals generated thereby to said tissue mass.

8. An electrosurgical generator according to claim 7, wherein $\zeta$ is substantially equal to 0.038.

9. An electrosurgical generator according to claim 7, wherein $\zeta$ is substantially equal to 0.025.

10. An electrosurgical generator according to claim 7, wherein said generating means has sufficient internal impedance to prevent electrosurgical cutting from occurring.

11. An electrosurgical generator according to claim 10, wherein said internal impedance is substantially equal to or greater than 1000 ohms at the fundamental frequency of operation.

12. An electrosurgical generator according to claim 10, wherein said internal impedance is substantially equal to or greater than 1000 ohms at the fundamental frequency of 500 kilohertz.

13. An electrosurgical generator for performing surgical operations on a tissue mass comprising,
an electrode for applying electrosurgical power to said tissue mass,
an electrical oscillator circuit comprising a capacitor and a transformer having a primary and a secondary winding, said capacitor being connected in parallel with said primary winding, said oscillator circuit having an open circuit Q factor of equal to, or greater than, 13,
means for repetitively exciting said oscillator circuit at a repetition rate substantially lower than the resonant frequency of said oscillator circuit to generate said electrosurgical power, and
means for coupling said oscillaor circuit to said electrode, so that said generator has an output impedance equal to, or greater than, 1000 ohms at the fundamental frequency of oscillation.

14. An electrosurgical generator according to claim 13 wherein said Q factor is substantially equal to 13.

15. An electrosurgical generator according to claim 14 wherein said output impedance is substantially equal to 2789 ohms at a fundamental frequency of 500 kilohertz.

16. An electrosurgical generator according to claim 13 wherein said Q factor is substantially equal to 20.

17. An electrosurgical generaor according to claim 16 wherein said output impedance is substantially equal to 1245 ohms at a fundamental frequency of 500 kilohertz.

18. An electrosurgical generator for performing surgical operations on a tissue mass comprising,
an active electrode for applying electrosurgical power to said tissue mass,
a timing signal source for generating timing signals,
an output transformer having a primary winding and a secondary winding, said secondary winding coupled to said active electrode,
a capacitor connected to said primary winding to form a parallel capacitance/inductance oscillator, and
means responsive to said timing signals for periodically exciting said oscillator at a frequency substantially less than the resonant frequency of said oscillator into open circuit damped oscillations, being substantially of the form $e^{-\zeta\omega_n t}\sin(\omega_n\sqrt{1-\zeta^2}t+\phi)$, where e is the base of the natural logarithm, $\omega_n$ is the undamped, natural frequency, $\zeta$ is the damping factor and is equal to or less than 0.038, but greater than 0 and $\phi$ is a phase angle.

19. An electrosurgical generator according to claim 18 wherein said generator further comprises a return electrode coupled to the secondary winding and the values of said capacitor and transformer are chosen to produce a sufficient output impedance between said active electrode and said return electrode to prevent electrosurgical cutting from occurring.

20. An electrosurgical generator according to claim 19 wherein said output impedance is substantially equal to 1245 ohms at a fundamental frequency of 500 kilohertz.

21. An electrosurgical generator according to claim 19 wherein said output impedance is substantially equal to 2789 ohms at a fundamental frequency of 500 kilohertz.

22. An electrosurgical generator according to claim 18 wherein said transformer has a powdered-iron toroidal core.

23. An electrosurgical generator according to claim 18 wherein said capacitor has a value of substantially 5.4 nanofarads.

24. An electrosurgical generator according to claim 18 wherein said capacitor has a value of substantially 2.5 nanofarads.

25. An electrosurgical generator according to claim 18 wherein said transformer has a primary:secondary turns ratio of 1:5.77.

26. An electrosurgical generator according to claim 18 wherein said transformer has a primary:secondary turns ratio of 1:9.5.

* * * * *